US00PP20968P2

(12) United States Plant Patent
Danziger

(10) Patent No.: US PP20,968 P2
(45) Date of Patent: Apr. 27, 2010

(54) ***BIDENS* PLANT NAMED 'DANYEL9'**

(50) Latin Name: *Bidens ferulifolia*
Varietal Denomination: DANYEL9

(75) Inventor: Gabriel Danziger, Moshav Nir-Zvi (IL)

(73) Assignee: Danziger "DAN" Flower Farm, Post Beit Dagan (IL)

( * ) Notice: Subject to any disclaimer, the term of this patent is extended or adjusted under 35 U.S.C. 154(b) by 0 days.

(21) Appl. No.: 12/381,472

(22) Filed: Mar. 12, 2009

(51) Int. Cl.
*A01H 5/00* (2006.01)

(52) U.S. Cl. ..... Plt./410

(58) Field of Classification Search ..... Plt./410
See application file for complete search history.

*Primary Examiner*—Annette H Para
(74) *Attorney, Agent, or Firm*—Foley & Lardner LLP

(57) ABSTRACT

A new distinct cultivar of *Bidens* plant named 'DANYEL9', characterized by its compact, ball-shaped (mounded) growth habit; freely branching habit with lateral flowering branches forming at every node; green in color, tripinnated leaves; high floriferous rate with large, eight petalled yellow flowers; and good resistance to pest and diseases.

2 Drawing Sheets

Latin name of the genus and species of the claimed plant: *Bidens ferulifolia.*

Variety denomination: 'DANYEL9'.

BACKGROUND OF THE INVENTION

The present invention relates to a new and distinct cultivar of *Bidens* plant, botanically known as *Bidens ferulifolia*, of the (Compositae) Asteracea family, commonly referred to as the Bur Marigold, and hereinafter referred to by the variety denomination 'DANYEL9'.

*Bidens*, of the Daisy family, (Compositae) Asteraceae, consists of hardy perennials and annuals, which are natively grown in southern climate zones in the U.S., Mexico and Guatemala.

The new *Bidens* 'DANYEL9' is a product of a planned breeding program conducted by the inventor, Gabriel Danziger, in Moshav Mishmar Hashiva, Israel. The objective of the breeding program was to develop a new *Bidens* cultivar with a compact growth habit and single, large in diameter flowers with a unique color combination.

The new *Bidens* 'DANYEL9' originated from a cross made in a controlled breeding program by the inventor, Gabriel Danziger, in 2007, in Moshav Mishmar Hashiva, Israel, from open pollination of the seed parent, *Bidens ferulifolia* 'CV-06-244' (unpatented), by an unknown *Bidens* cultivar. The new *Bidens* 'DANYEL9' was discovered and selected by the inventor, Gabriel Danziger, as a single flowering plant within the progeny of the stated cross in a controlled environment in Moshav Mishmar Hashiva, Israel.

Asexual reproduction of the new *Bidens* 'DANYEL9' by vegetative cuttings was first performed in June of 2007 in Moshav Mishmar Hashiva, Israel, and has demonstrated that the combination of characteristics as herein disclosed for the new cultivar are firmly fixed and retained through successive generations of asexual reproduction. The new cultivar reproduces true-to-type.

SUMMARY OF THE INVENTION

The following traits have been repeatedly observed and are determined to be the unique characteristics of 'DANYEL9' which in combination distinguish this *Bidens* as a new and distinct cultivar:

1. compact, ball-shaped (mounded) growth habit;
2. freely branching habit with lateral flowering branches forming at every node;

3. green in color, tripinnated leaves;
4. high floriferous rate with large, eight petalled yellow flowers; and
5. good resistance to pest and diseases.

Since the new *Bidens* 'DANYEL9' originated from open pollination of the seed parent, *Bidens ferulifolia* 'CV-06-244' (unpatented), by an unknown *Bidens* cultivar, a botanical comparison can only be provided between plants of the new *Bidens* 'DANYEL9' and the seed parent, 'CV-06-244', as is described in Table 1.

TABLE 1

| Characteristic | New Cultivar 'DANYEL9' | Female Parent '06-244' (unpatented) |
|---|---|---|
| Plant shape: | Compact, ball-shaped (mounded) | Vigorous, semi-trailing |
| Plant size: | Height: About 23 cm<br>Spread: About 45 cm | Height: About 25 cm<br>Spread: About 70 cm |
| Inflorescence size: | Depth: About 0.5 cm<br>Diameter: About 4 cm | Depth: About 0.5 cm<br>Diameter: About 3 cm |
| Inflorescence color | Yellow with golden eye | Yellow with golden eye |
| Leaf size: | Length: About 2.5 cm<br>Width: About 2 cm | Length: About 4 cm<br>Width: About 3 cm |
| Leaf color: | Green, RHS 137 A | Green, RHS 137 A |
| Internode Length: | About 2 cm to 3 cm | About 3 cm to 4 cm |

Of the many commercial cultivars known to the present inventor, the most similar in comparison to the new *Bidens* 'DANYEL9' is the *Bidens* 'Yellow Glow' (unpatented), as is described in Table 2:

TABLE 2

| Characteristic | New Cultivar 'DANYEL9' | Comparison Cultivar 'Yellow Glow' (unpatented) |
|---|---|---|
| Plant shape: | Compact, ball-shaped (mounded) | Vigorous, semi-trailing |
| Plant size: | Height: About 23 cm<br>Spread: About 45 cm | Height: About 28 cm<br>Spread: About 65 cm |
| Inflorescence size: | Depth: About 0.5 cm<br>Diameter: About 4 cm | Depth: About 0.3 cm<br>Diameter: About 3.5 cm |

TABLE 2-continued

| Characteristic | New Cultivar 'DANYEL9' | Comparison Cultivar 'Yellow Glow' (unpatented) |
|---|---|---|
| Inflorescence color | Yellow with golden eye | Yellow with golden eye |
| Leaf size: | Length: About 2.5 cm<br>Width: About 2 cm | Length: About 3.5 cm<br>Width: About 3 cm |
| Leaf color: | RHS Green 137 A | RHS Green 137 B |
| Internode Length: | About 2 cm to 3 cm | About 3 cm to 4.5 cm |

BRIEF DESCRIPTION OF THE PHOTOGRAPHS

The accompanying photographs illustrate the overall appearance of the new *Bidens* 'DANYEL9' showing the colors as true as is reasonably possible with colored reproductions of this type. Colors in the photographs may differ slightly from the color value cited in the detailed botanical description which accurately describe the color of 'DANYEL9'.

DETAILED BOTANICAL DESCRIPTION

Figure 1:
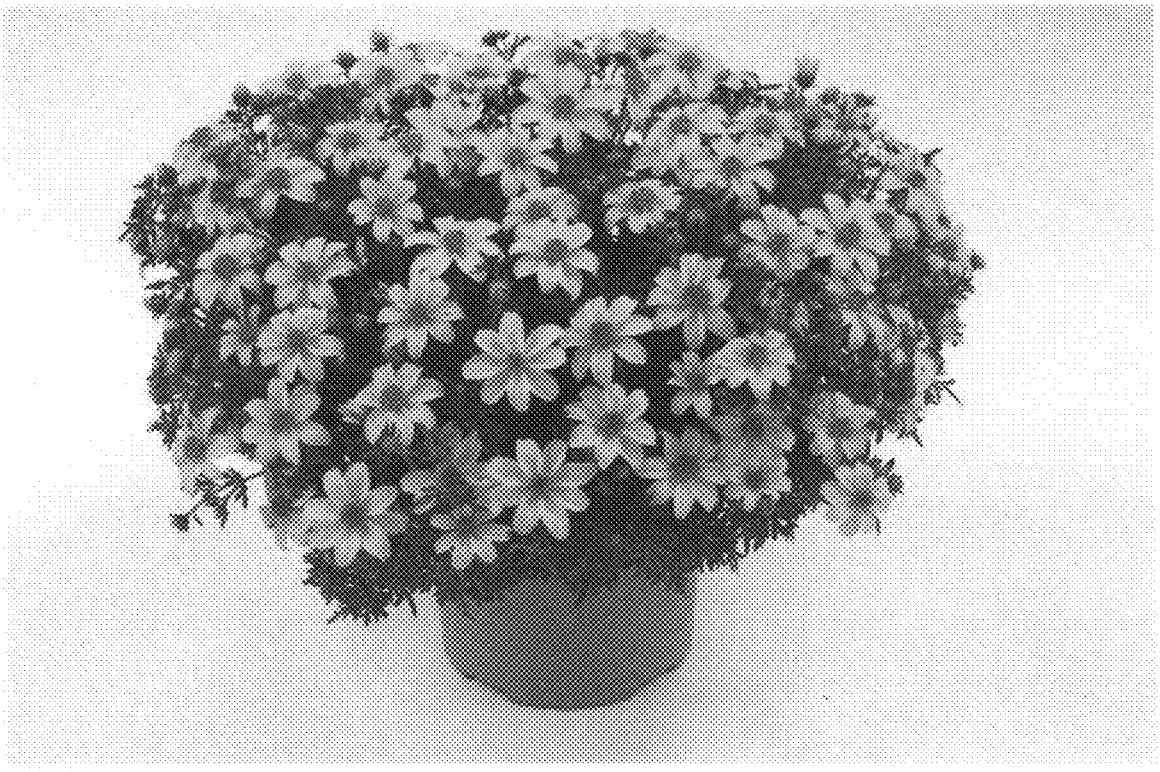
FIG. 1 shows a side view perspective a typical flowering plant of 'DANYEL9' in a 13 cm pot, at three months of age.
Figure 2:
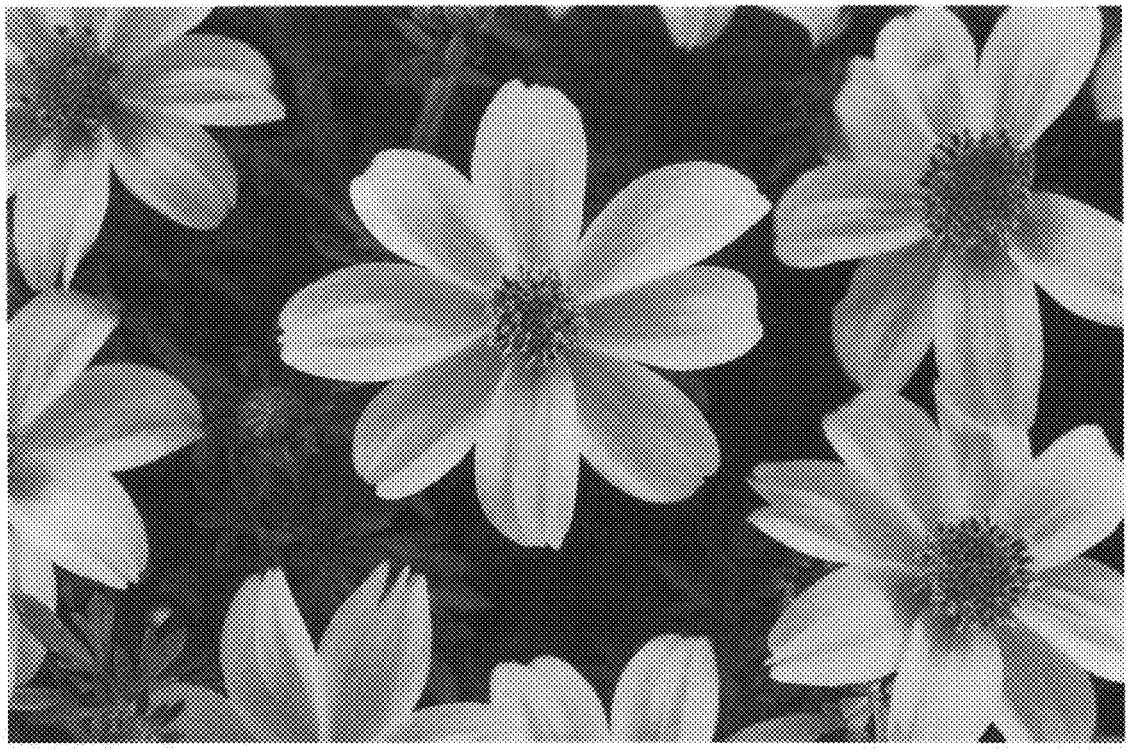
FIG. 2 shows a close-up view of the typical flowers, buds and leaves of 'DANYEL9' at three months of age.

The new *Bidens* 'DANYEL9' has not been observed under all possible environmental conditions. The phenotype of the new cultivar may vary with variations in environment such as temperature, light intensity, and daylength, without any change in the genotype of the plant.

The aforementioned photographs, together with the following observations, measurements and values describe plants of the new *Bidens* 'DANYEL9' as grown in a greenhouse in Moshav Mishmar Hashiva, Israel, under conditions which closely approximate those generally used in commercial practice.

Plants of 'DANYEL9' are grown outdoors in a moderate climate, and grown indoors during the winter. Irrigation and fertilization are needed on a regular basis. For optimal growth, grow plants of 'DANYEL9' in full sunlight. Plants of 'DANYEL9' are fully-grown in 3 months when grown in full sunlight, and bloom all year-round in a moderate climate.

Color references are made to The Royal Horticultural Society Colour Chart (R.H.S.), 2001 Edition, except where general colors of ordinary significance are used. Color values were taken under daylight conditions at approximately 12:00 noon in Moshav Mishmar Hashiva, Israel. The age of the plant described is three months.

Botanical classification: *Bidens ferulifolia*.

Parentage:

*Seed parent.*—*Bidens ferulifolia* '06-244' (unpatented).

*Pollen parent.*—Open pollination by unknown *Bidens* cultivar.

Optimal growth conditions:

*Light intensities.*—Full sunlight.

*Temperature.*—Day: 18° C. to 24° C. Night: 13° C. to 18° C.

*Temperature tolerance.*—Tolerant to a low temperature of about 5° C. and tolerant to a high temperature of about 35° C.

*Fertilization.*—A balanced fertilizer with level of 100 ppm Nitrogen.

*Growth regulators.*—Unnecessary.

Propagation:

*Type.*—Vegetative terminal cuttings.

*Time and temperature to initiate roots.*—About 5 to 6 days at 18° C. to 20° C.

*Time and temperature to produce a rooted cutting.*—About 9 to 12 days at 18° C. to 20° C.

*Rooting habit.*—Fine, freely branching and dense.

*Root color.*—White, RHS 155A.

Plant description:

*General appearance and form.*—Perennial plant with mounding growth habit.

*Growth and branching habit.*—Freely branching with lateral flowering branches forming at every node, mounded. One pinch is required.

*Growth rate/vigor.*—Medium vigor.

*Plant height.*—About 23 cm.

*Plant width* (*spread*).—About 45 cm.

*Plant strength.*—Sturdy.

*Crop time to produce a mature flowering plant.*—After rooting, about 6 to 8 weeks are required to produce finished flowering plants in 10–12 cm pots.

Branches:

*Number of branches per plant.*—About 8 primary, about 50 secondary.

*Length.*—Primary: About 20 cm. Secondary: About 15 cm (including flower).

*Diameter.*—Primary: About 0.4 cm. Secondary: About 0.2 cm.

*Internode length.*—Primary: About 1.5 cm. Secondary: About 1 cm.

*Aspect.*—Primary: initally upright then bending outwardly. Secondary: upright.

*Texture.*—Primary: Slightly velvety. Secondary: Velvety.

*Pubescence.*—Primary: Slightly. Secondary: Pubescent with white, fine hair.

*Color.*—Primary: Upper surface: Yellow-Green, RHS 146B. Under surface: Yellow-Green, RHS 146B. Secondary: Upper surface: Yellow-Green, RHS 146C. Under surface: Yellow-Green, RHS 146C.

Foliage description:

*Arrangement.*—Opposite.

*Length.*—About 3.5 cm.

*Width.*—About 2.5 cm.

*Overall shape of leaf.*—Tripinnated.

*Shape at apex.*—Acute.

*Shape at base.*—Acute.

*Margin.*—Entire.

*Texture.*—Upper and under surfaces: Smooth.

*Pubescencce.*—Upper and under surfaces: None.

*Color of developing foliage.*—Upper surface: Green, RHS 137A. Under surface: Green, RHS 137C.

*Color of mature foliage.*—Upper surface: Green, RHS 137B. Under surface: Green, RHS 137D.

*Venation pattern.*—Palmate.

*Venation color.*—Upper surface: Green, RHS 137B. Under surface: Green, RHS 137A.

*Petiole length.*—About 1.0 cm.

*Petiole diameter.*—About 0.1 cm.

*Petiole texture.*—Upper and under surfaces: Velvety.

*Petiole color.*—Upper surface: Green, RHS 137D. Under surface: Green, RHS 137D.

*Foliage fragrance.*—None.

Inflorescence description:

*Appearance.*—Daisy-type, composite inflorescence form. Disc and ray florets develop acropetally on capitulum.

*Natural flowering season.*—All year round in moderate climate. Flowering occurs all year round outdoors in Israel.

*Flowering response time.*—About 6 weeks from planting.

*Flowering longevity.*—On the plant: Flowering of a single flower lasts about 10 days.

*Fragrance.*—Subtle sweet fragrance.

*Quantity of inflorescences and buds per plant.*—About 200 to 300.

*Bud* (*about* 1 *to* 2 *days prior to opening*).—Length: About 1.3 cm. Diameter: About 0.7 cm. Shape: Ovoid. Color: Apex: Yellow, RHS 13A. Base: Yellow-Green, RHS 147A. Texture: Velvety.

*Inflorescence.*—Type: Solitary. Form: Daisy-like. Symmetry: Symmetric. Orientation at opening: Slanted upward. Size (including ray and disc florets): Depth (height): About 0.5 cm. Diameter About 4.0 cm. Disc diameter: About 0.8 cm.

*Ray florets.*—Quantity per inflorescence: 8 in a single whorl. Length: About 1.7 mm. Width: About 0.9 mm. Overall shape: Elliptic. Shape at apex: Tri-dentate. Shape at base: Obtuse. Margin: Entire. Texture: Upper and under surfaces: Velvety. Orientation: Initially 0° from vertical, with development, close to 90° from vertical. Color (when opening): Upper surface: Yellow, RHS 13A. Under surface: Yellow, RHS 13A. Color (when fully opened): Upper surface: Yellow, RHS 9A. Under surface: Yellow, RHS 9B.

*Disc florets.*—Quantity per inflorescence: About 50 to 60. Length: About 7 mm. Width: About 1 mm. Overall shape: Tubular. Shape at apex: Toothed. Shape at base: Fused. Margin: Entire. Texture: Upper and under surfaces: Velvety. Color (when opening): Upper surface: Yellow-Green, RHS 152B. Under surface: RHS Yellow-Green 153D. Color (when fully opened): Upper surface: Yellow-Orange, RHS 14A. Under surface: Yellow, RHS 2A.

*Phyllaries.*—Quantity: About 1 to 2. Attachment: About 1 to the receptacle bottom and about 1 near ray florets. Length: About 7 mm to 8 mm. Width: About 2 mm. Overall shape: Lanceolate. Shape at apex: Acute. Shape at base: Acuminate. Margin: Entire. Texture: Upper and under surfaces: Velvety. Color: Upper surface: Green, RHS 137A. Under surface: Green, RHS 137B. Anythocyanin pigmentation of phyllaries limb: Absent.

*Peduncle.*—Aspect: Upright, stong. Length: About 2.0 cm. Diameter: About 1.0 mm. Angle: About 30° from vertical. Texture: Velvety. Color: Green, RHS 137A.

Reproductive organs:

*Androecium* (*on disc florets only*).—Stamens: Number: 5 (fused as tube). Arrangement: Didynamous. Type: Basifixed. Dehiscence of stamens. Extrose. Length: About 5.0 mm. Color: Yellow-Orange, RHS 17A. Anthers: Shape: Rounded. Length: About 0.5 mm. Color: Yellow-Orange, RHS 17A. Filaments: Length: About 4.0 mm. Color: Yellow, RHS 5A. Pollen: Amount: Moderate. Pollen color: Yellow-Orange, RHS 17A. Pollination requirements: None.

*Gynoecium* (*on ray and disc florets*).—Pistils: Quantity per inflorescence: About 50. Length: About 7.0 mm. Stigma: Shape: Bifurcate. Width: About 0.5 mm. Color: Yellow-Orange, RHS 15A. Style: Shape: Terete. Length: About 6.0 mm. Ovary: Quantity: One per pistil. Shape: Ellipsoid. Position: Superior. Length: About 1.0 mm. Width: About 0.3 mm. Color: Green-Yellow, RHS 1D.

Seeds: Quantity per fruit: About 30. Shape: Oblong. Length: About 8.0 mm. Width: About 0.5 mm. Texture: Rough. Color: Brown, RHS N200A.

Fruit: None, the seeds are borne exposed, attached by their bases to the receptacle.

Disease/pest resistance: Resistance to disease and pests common to *Bidens* has not been tested on plant grown under commercial conditions.

Disease/pest susceptibility: Susceptibility to disease and pests common to *Bidens* has not been observed on plant grown under commercial conditions.

Temperature tolerance: Plants of the new *Bidens* have exhibited good tolerance to draught, rain and wind, however, flowering may cease during hot periods (temperatures above 35° C.). Low temperature tolerance to 5° C.

What is claimed is:

1. A new and distinct cultivar of *Bidens* plant named 'DANYEL9', as illustrated and described herein.

* * * * *